United States Patent [19]

Lizzi et al.

[11] Patent Number: 4,858,124
[45] Date of Patent: Aug. 15, 1989

[54] METHOD FOR ENHANCEMENT OF ULTRASONIC IMAGE DATA

[75] Inventors: Frederic L. Lizzi, Tenafly; Mykola M. Yaremko, Hoboken, both of N.J.; Ronald H. Silverman, Brooklyn, N.Y.; D. Jackson Coleman, Haworth, N.J.

[73] Assignee: RiverSide Research Institute, New York, N.Y.

[21] Appl. No.: 85,289

[22] Filed: Aug. 11, 1987

Related U.S. Application Data

[63] Continuation of Ser. No. 641,015, Aug. 15, 1984, abandoned.

[51] Int. Cl.$^4$ ............................................. G06F 15/42
[52] U.S. Cl. .................................... 364/413.01; 73/602
[58] Field of Search ...................... 364/414.5; 128/660, 128/653; 73/602

[56] References Cited

U.S. PATENT DOCUMENTS

| | | |
|---|---|---|
| 4,228,804 | 10/1980 | Holasek et al. . |
| 4,270,546 | 6/1987 | Perilhou ............................ 73/602 X |
| 4,428,235 | 1/1984 | Sugiyama ........................ 73/602 X |
| 4,428,237 | 1/1984 | Zeger et al. ..................... 73/602 X |
| 4,501,149 | 2/1985 | Konno ............................... 73/602 X |
| 4,511,984 | 4/1985 | Sumino ............................. 364/415 |
| 4,561,019 | 12/1985 | Lizzi et al. . |
| 4,564,018 | 1/1986 | Hutchinson ...................... 128/660 |
| 4,575,799 | 3/1986 | Miwa et al. ..................... 364/414 |

Primary Examiner—E. A. Goldberg
Assistant Examiner—Lincoln Donovan
Attorney, Agent, or Firm—Brumbaugh, Graves, Donohue & Raymond

[57] ABSTRACT

Methods for enhancement of data obtained from scanning objects such as body tissue with ultrasonic wideband pulses to detect characteristics of the tissue and to identify the tissue. The methods include performing spectral analysis on selected time portions of signals obtained from ultrasonic scanning to derive spectral data which is representative of the received signal characteristics for spatial samples of a particular region of interest in the body. The characteristic values are selected to correlate with significant characteristics of the material. A display of the selected body region is generated, with the display characteristic for each of the spatial samples being selected in accordance with the derived spectral characteristic values. Examples of the spectral characteristic values include spectral amplitude, spectral slope, and spectral amplitude uncertainty. The spectral characteristic data can be used to derive periodicity data, such as cepstral data or spatial-correlation data, for each of the spatial samples. The spectral characteristic data obtained can be compared to data for tissue having known tissue characteristics to identify the tissue type. Related means for suppressing the display of noise, characterizing tissues using discriminent functions based on spectral data, and estimating scatter sizes are also shown.

43 Claims, 11 Drawing Sheets

METHOD FOR ENHANCEMENT OF ULTRASONIC IMAGE DATA

This invention was made with Government support under grant numbers EY 03183 and EY 01212 awarded by the National Institutes of Health. The Government has certain rights in this invention.

This application is a continuation of application Ser. No. 641,015, filed on 8/15/84, now abandoned.

BACKGROUND OF THE INVENTION

This invention relates to a method for processing reflected ultrasonic signals from body tissue to obtain information concerning the nature of the body tissue which can be used in connection with diagnosis of a tissue disorder, such as a malignant growth.

Ultrasonic imaging, wherein wideband pulses of ultrasonic signals are transmitted into body tissue and received from body tissue for purposes of forming an image representing a cross-section through a particular body tissue of interest, has been known and used in medical applications, and has particular applications to examination of eye tissue, which cannot easily be examined by X-ray or by surgical techniques.

Images derived from ultrasonic scattering, often called A-scan and B-scan images, give a representation of acoustic signal amplitude as the signal pulses are reflected by various structures within the body tissue being examined. Displays based on the reflected signal amplitude can in some cases by useful for providing the physician with information concerning the location and size of an abnormal tissue growth, but great skill may be required in attempting to determine what type of tissue growth is present in view of an amplitude reflection display.

It is an object of the present invention to provide methods for further analyzing reflected ultrasonic signals from body tissues or other material to determine from the analysis of the reflected signals additional information concerning the structure from which the signals were reflected.

SUMMARY OF THE INVENTION

In accordance with one aspect of the present invention there is provided a method for processing reflected acoustic signals from a body of material and for generating a display of at least a portion of the body which is representative of characteristics of the material that are not typically displayed in conventional A-scan or B-scan systems. The method includes transmitting acoustic signals into a region of interest in the body in an ordered spatial progression and receiving reflected acoustic signals from the body. A spectral analysis is performed on selected time portions of the received signal to derive spectral data which is representative of received signal characteristics for spatial samples of the body within the region of interest. The spatial samples correspond to time portions of the received signal. Spectral characteristic values are derived from the spectral data for each of the spatial samples. The characteristic values are selected to correlate with significant characteristics of the material. A display is generated of the body region of interest with the display characteristic for each of the spatial samples being selected in accordance with the derived spectral characteristic values.

Examples of the spectral characteristic values include spectral amplitude, spectral slope and spectral amplitude uncertainty. The results of the spectral analysis are typically a set of values indicative of spectral power which is a function of frequency for each selected time interval portion. These spectral power values may be normalized to spectral power values which are determined by reflecting the acoustic signal from an object having known reflection characteristics. The spectral characteristic values may be combined to generate combined spectral characteristic values which may correlate with significant material characteristics. The method has particular application to processing of reflected ultrasonic signals from body tissue and has particular application when the body tissue being examined consists of the eye.

In accordance with another aspect of the present invention the spectral characteristic data can be used to derive periodicity data for each of the spatial samples. The periodicity data may be cepstral data or may be spatial-correlation function data. In accordance with still another aspect of the present invention periodicity data may be derived directly from selected time portions of the received signal.

In accordance with another aspect of the present invention spectral characteristic data for time interval portions of the received signal which correspond to the spatial samples of the tissue within the region of interest can be compared to spectral characteristic data for tissue having known tissue characteristics. In this case a display can be generated which indicates tissue types by reference to the derived correlation values.

In accordance with another aspect of the present invention there is provided a method for analyzing tissue characteristics. This method includes transmitting ultrasonic signals into the tissue and receiving reflected ultrasonic signals from the tissue. The received signals are divided into signal time periods which are representative of ultrasonic signals reflected from regions of increasing depths in the tissue. The signals for each of the signal time periods are analyzed to derive spectral data representative of spectral characteristics for each of the signal time periods. The spectral data is analyzed to derive values representative of spectral slope for each of the signal time periods. The spectral slope values are analyzed to define a linear function which is representative of the variation in spectral slope as a function of depth in the tissue. The dispersion of the spectral slope values from the linear function is determined. This dispersion can be a clinically significant feature in the course of analyzing the properties of certain tissues. In particular, the maximum positive deviation of slope values from the linear function can be of clinical significance.

In accordance with another aspect of the present invention there is provided a method for suppressing noise in the displays which are generated by transmitting and receiving ultrasonic signals in materials. A received signal is divided into time sequential signal samples and a spectral analysis of the signal samples is performed to derive spectral data representative of received spectral characteristic of the samples. The spectral data are further analyzed to derive values of spectral energy at a number of frequencies and spectral amplitude and spectral slope for each of the samples. The values of spectral amplitudes and spectral slope are compared to values which are characteristic of noise and a noise representative signal is generated for signal samples which have values within a selected range of the noise characteristic values. For these signal samples a fixed selected image characteristic, such as a blank display, is provided in the corresponding spatial samples in the image.

In accordance with another aspect of the present invention there is provided a method of identifying tissue type within a region of interest of body tissue wherein a spectral analysis is performed on the received signal to derive spectral data and the spectral data are analyzed to derive at least two spectral characteristic values. A discriminant function is computed from the spectral characteristic values according to a formula which is selected to provide discrimination among tissue types based on spectral characteristic values for signals reflected from tissue having known tissue types. In this way the tissue can be identified on the basis of the value of the discriminant function.

An improvement on the foregoing method involving identification of tissue type using a discriminant function is the use of more than one discriminant function.

In accordance with another aspect of the present invention there is provided a method for determining an estimate of effective average size of scattering particles in a body of material. This method includes transmitting acoustic signals into a material and receiving reflected acoustic signals from at least a portion of the material. The received reflected signals are analyzed to derive spectral data representative of spectral characteristics of the reflected signals. The spectral data is analyzed to derive spectral slope values and an average effective particle size is computed from the spectral slope values using a formula relating particle size to spectral slope.

Another aspect of the invention involves repeating the steps of one or more of said methods described above at at least two different times, and then comparing the results thereof to detect any changes in characteristics in the body. This aspect has particular application to detecting changes in the human body as a result of medical treatment.

For a better understanding of the present invention, together with other and further objects, reference is made to the following description, taken in conjunction with the accompanying drawings, and its scope will be pointed out in the appended claims.

BRIEF DESCRIPTION OF THE DRAWINGS

FIG. 16B showing a malignant melanoma stain image; and FIG. 16C showing a metastatic carcinoma stain image.

FIG. 17A showing a B-scan image; FIG. 17B showing a malignant-melanoma stain image; and FIG. 17C showing a metastatic-carcinoma stain image.

DESCRIPTION OF THE INVENTION

Figure 1:
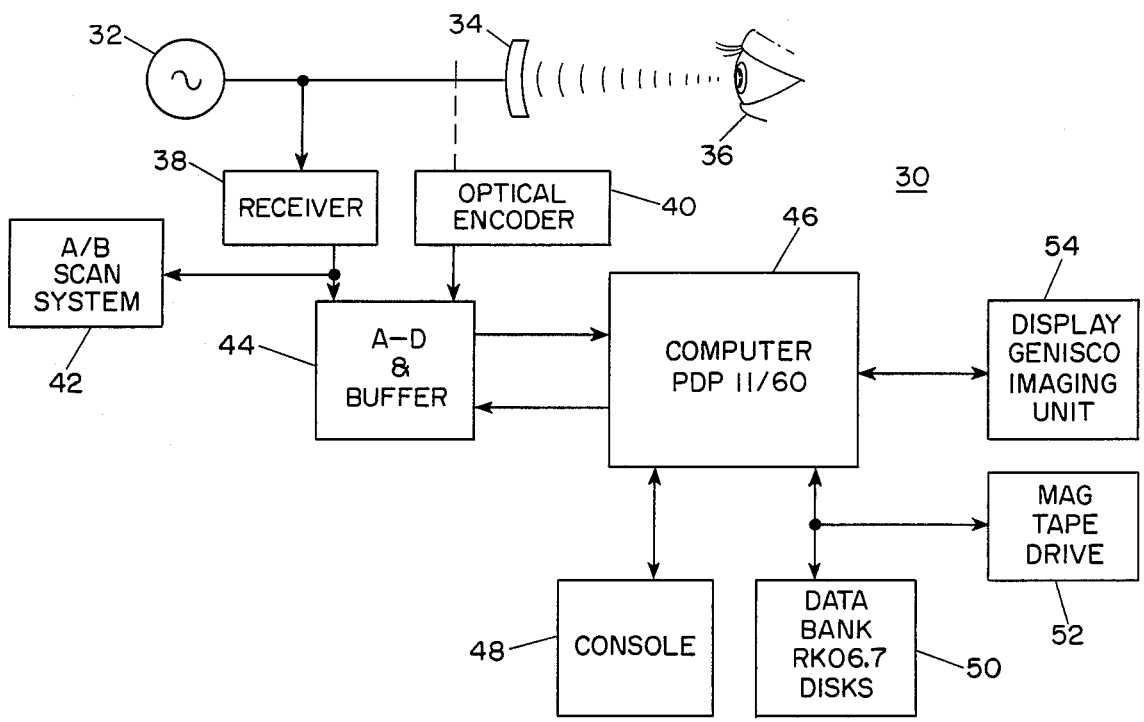
FIG. 1 is a block diagram of a system for carrying out the methods of the present invention.

Referring to FIG. 1 there is shown in block diagram form a system which is useful for carrying out the methods of the present invention. The ultrasonic diagnostic system 30 illustrated in FIG. 1 includes a transmitter 32 which generates wideband acoustic pulses having a frequency range from 5 to 15 MHz. These pulses are transmitted through transducer 34 into a body of material, such as body tissue which is represented in FIG. 1 by a patient's eye 36. As is known to those skilled in the art, it is conventional to immerse transducer 34 into a fluid body, such as saline solution, so that the ultrasonic signals are conveniently transmitted through the saline solution into the eye of the patient.

Figure 4:
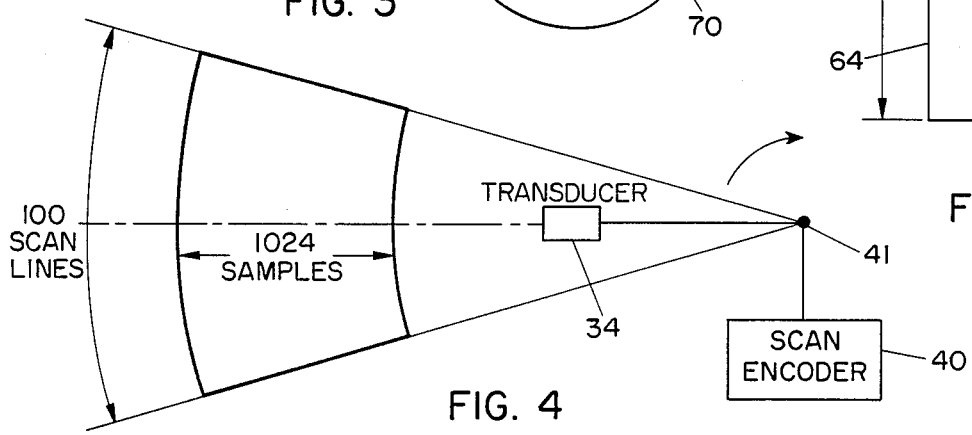
FIG. 4 is a diagram illustrating a transducer arrangement for scanning a region of interest in body tissue.

Transducer 34 is preferably arranged to be movable in one angular coordinate as shown in FIG. 4. FIG. 4 illustrates a transducer assembly 34 which is pivoted about pivot point 41. The angular orientation is sensed by scan encoder 40, thereby indicating the orientation of the transducer 34. The scan encoder 40 outputs a pulse each time the transducer 34 is moved a predetermined angular increment. This pulse is supplied to the analog-to-digital (A-D) converter and buffer 44 as shown in FIG. 1. Each pulse initiates the acquisition of radio frequency (RF) data from a single scan line segment.

Figure 2:
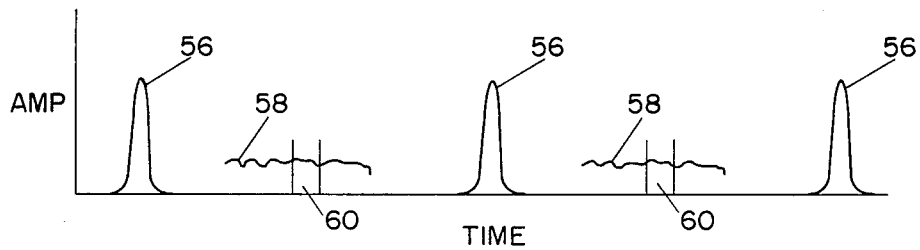
FIG. 2 is a diagram illustrating signals used in connection with transmission and reception of ultrasonic signals in the system of FIG. 1.
Figure 3:
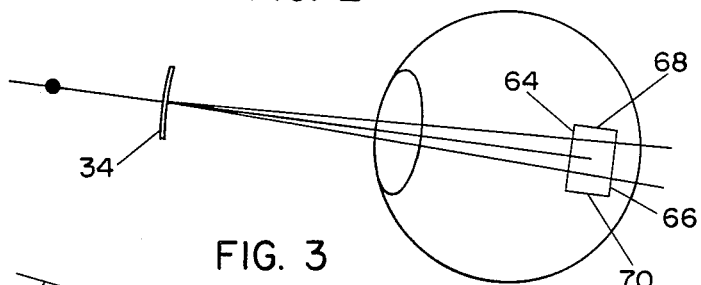
FIG. 3 is a diagram illustrating the scanning of ultrasonic signals through a region of interest in an eye.

As noted in FIG. 3, the region of interest of a tumor within an eye is bounded by range values 64 through 66, which may correspond to the focal region of transducer 34. FIG. 2 illustrates transmitted pulses 56 which originate from transducer 34 and received reflected signals 58. When the transducer 34 is properly oriented there is a region of interest of the signal which corresponds to signal portions 60 shown in FIG. 2. Signal portion 60 is the time interval of the signal which corresponds to the transmission time which defines reflections from boundaries 64 and 66.

Figure 5:
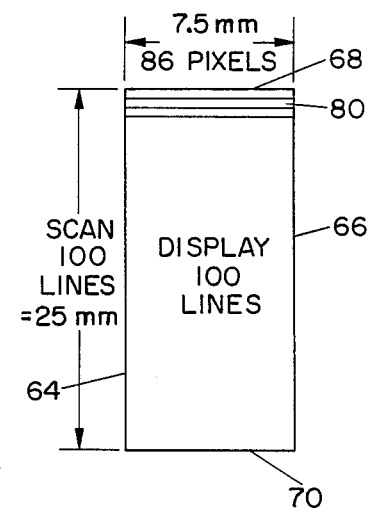
FIG. 5 is a diagram illustrating the details of a scan region of interest.

Signals which results from reflections within the region of interest shown in FIG. 3 are transferred to A-D converter and buffer 44 shown in FIG. 1 wherein the signals are digitized at a sampling rate of 100 MHz. Details of this region, wherein reflected signals are digitized, are shown in FIG. 5. In the vertical direction the region is divided into 100 lines, each of which corresponds to an acoustic path through the region of interest. This region is vertically shown to be approximately 25 millimeters. In the horizontal direction, which corresponds to the direction of acoustic signal transmission, the range is 7.5 millimeters and corresponds to 1,024 signal samples. These samples are eventually processed to result in 86 pixels on a display, using approximately 12 digital samples for generation of each display pixel as will be further described. In the transverse, vertically illustrated direction of FIG. 5 the display can be generated with 100 display scan lines so that the entire display of the image which is generated would be 86 by 100 pixels, each of which will generated using special techniques as will be further described.

As previously mentioned the RF signals 58 which are reflected from the tissue 36 are provided to a receiver 38 thereafter to A-D converter and buffer 44. As indicated, only portions of the signal 60, which correspond to a region of interest, are provided for digitization. The entire RF signal may also be supplied from receiver 38 to a conventional A-scan and B-scan display system 42. The A-scan and B-scan display system may be particularly useful for selecting portions of eye tissue which are to be scanned for purposes of digitization, and for providing the examining physician with a conventional ultrasonic image of the eye while he is undertaking the examination.

The digitized information regarding reflection of ultrasonic signals from eye 36 are provided to computer 46 by A-D converter and buffer 44. These data can be processed immediately or may be stored on disks in a data bank 50 for later processing. The present invention involves several details of the data processing, which result in the generation of images on display unit 54 which indicate significant characteristics of the tissue structure which can be determined from the characteristics of the digitized reflected ultrasonic signals. The system 30 illustrated in FIG. 1 also includes a control console 48 which includes operator controls for selecting the particular signal analysis desired as well as data bank 50 which contains in addition to the information derived from the current patient other information on reflected acoustic signals from patients having known tissue abnormalities. A magnetic tape drive 52 is also provided for long term storage of this data.

Figure 6:
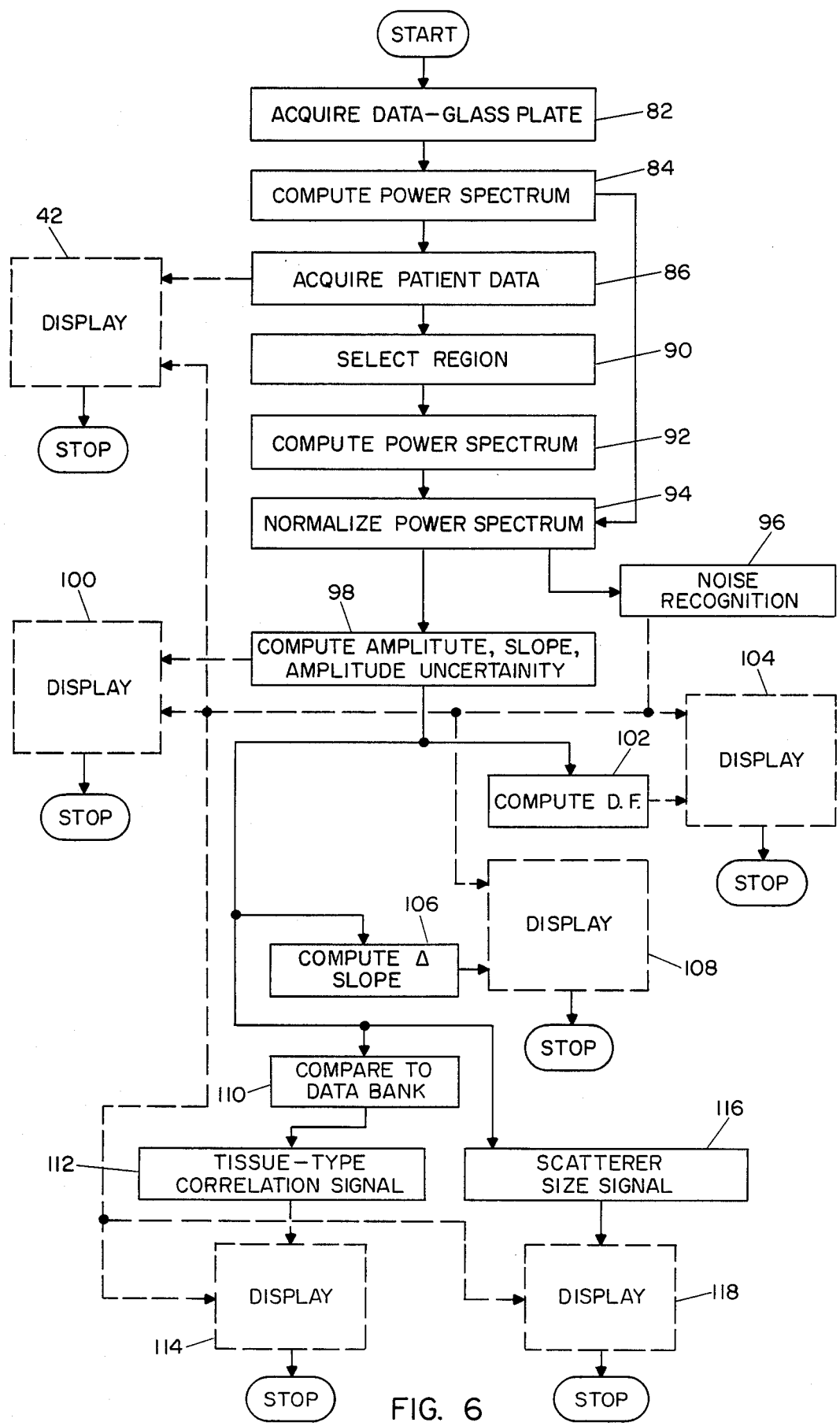
FIG. 6 is an overall program flow diagram relating to the methods of the present invention.

FIG. 6 is an overall program flow diagram illustrating the various methods of signal processing for generating images or generating derived data useful in diagnosing tissue disorders in accordance with the present invention.

Prior to acquiring data on reflected ultrasonic signals from tissue or other material, the system of FIG. 3 is calibrated by acquiring reflection data from an object having known reflection characteristics. One such object is a planar glass plate, which maybe immersed in the saline solution containing transducer 34, and spaced at a distance from transducer 34. This distance corresponds to the distance used in acquiring tissue data, and is typically close to the focal region of the transducer.

Referring now to FIG. 6, the power spectrum of the reflections of ultrasonic signals from the glass plate is computed at step 84. The results of this computation provide an indication of the spectral characteristics of transmitter 32 and transducer 34 as well as receiver 38, which can be used for purposes of normalizing the spectrum of signals reflected from tissue. Following the acquisition of normalizing data, patient data maybe acquired at step 86. Those skilled in the art will recognize that normalizing data may also be acquired following the acquisition of patient data. During the acquisition of patient data, a display on a conventional system 42 may be provided. This display will be helpful to the physician in identifying the region of tissue which he wishes to more closely examine, such as a tumor within the eye.

At step 90 the physician selects the region of interest for purposes of further analysis. This region may be selected from any of the scanned tissue planes from which data was acquired. Using console 48, the physician may designate a relatively small area of tissue for analysis, such as the 7.5 millimeter by 25 millimeter region indicated in FIG. 5. Even smaller regions may be selected for analysis.

Figure 7:
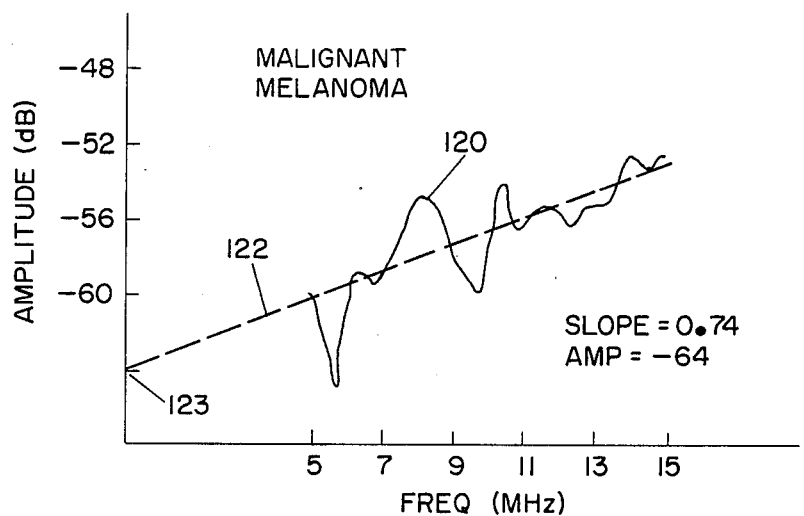
FIG. 7 is a graph showing spectral amplitude as a function of frequency for signals reflected from malignant melanoma.
Figure 8:
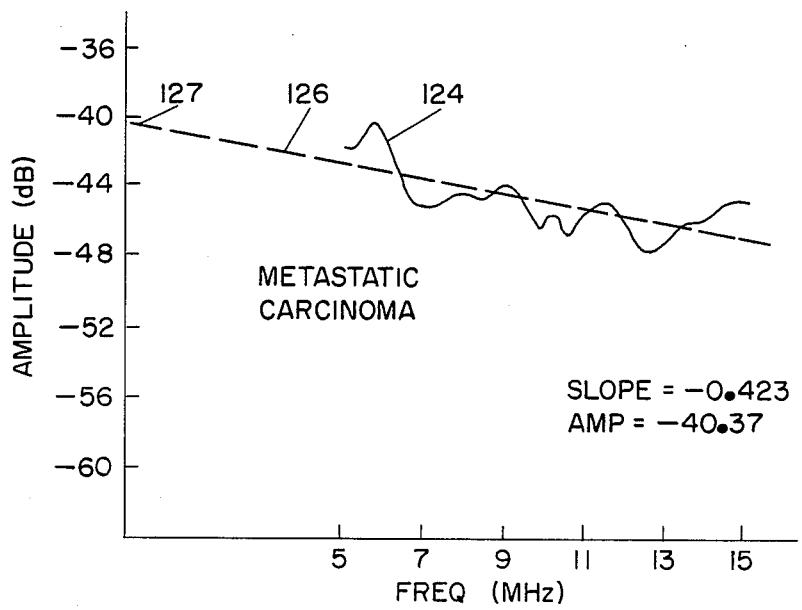
FIG. 8 is a graph showing spectral amplitude as a function of frequency for signals reflected from metastatic carcinoma.
Figure 10:
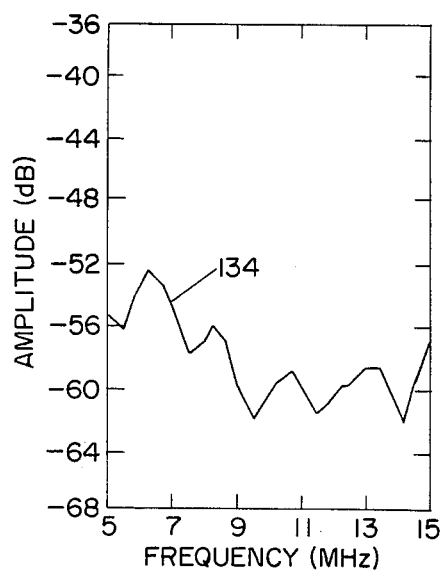
FIG. 10 is a diagram of spectral amplitude as a function of frequency for a subretinal hemorrhage.

The digitized data acquired at step 86 is provided to computer 46 which performs a power spectral analysis at step 92. This spectral analysis is performed by taking the fast Fourier transform (FFT) of samples of the digitized reflected signal. Typically, 128 digital samples of the received signal are used for forming the power spectrum calculation at step 92. At step 94 each of the power spectra derived at step 92 is normalized using the computed power spectrum for the glass plate target at approximately the same distance from the transducer, computer at step 84, as described above, also using a fast Fourier transform. The result is a normalized power spectrum for each selected time portion of the received signal which corresponds to a spatial sample of the material which is being examined. The normalized power spectrum may have approximately 20 independent values of signal power as a function of frequency within the frequency band 5 to 15 MHz. FIGS. 7, 8 and 10 are examples of curves drawn from such spectrum analysis which are normalized using the glass plate or another target having known reflection characteristics.

Referring to FIG. 7, the power spectrum curve 120 for a particular sample of tissue known to be malignant melanoma is shown. The amplitude is scaled in decibels (dB) with respect to the calibration target spectrum. Line 122 is a linearized approximation to the plot of spectral data. This linearized approximation is derived from the actual spectral data using conventional linear regression analysis techniques independently for each time portion of the received signal corresponding to a spatial sample of the material. Two useful properties of linearized approximations are their slope with respect to frequency and their frequency specific normalized spectral amplitude usually specified at the zero frequency intercept. Linear approximation 122 has a characteristic slope, which in this particular case is 0.74 dB per MHz, and a characteristic zero frequency intercept amplitude, which in this case is −64 dB. In addition to these values of the linearized spectrum characteristic 122, there is an amplitude uncertainty, which can be computed, and which results from irregularities or curvature of the actual spectral characteristic 120. Such uncertainty arises out of either rapid fluctuations of the amplitude spectral characteristic 120 or out of a curvature of the spectral characteristic.

The present inventors have discovered that the spectral slope, amplitude frequency specific normalized spectral and amplitude uncertainty characteristics of the power spectrum linearization can have an indication as to certain clinically significant characteristics of the tissue which generated the reflection signals from which the spectral characteristics were derived. In this respect, attention is directed to a comparison of FIG. 7 with FIG. 8.

FIG. 8 is a spectral amplitude curve 124 which has been derived from ultrasonic signals reflected from a metastatic carcinoma. This spectrum has been linearized into line 126 which has a zero frequency intercept 127 at an amplitude of −40.37 dB and a slope of −0.423 dB per MHz. A comparison of the linearization 122 of curve 120 and the linearization 126 of curve 124 shows significantly different spectral characteristic values for the two different tissue types. It is seen that the slope characteristic is much lower for the metastatic carcinoma tissue and the amplitude characteristic is much higher for the metastatic carcinoma tissue.

Applying this discovery to the method of the present invention, at step 98 the frequency specific normalized spectral amplitude, spectral slope and amplitude uncertainty of the power spectrum for each spatial sample of the tissue, corresponding to a time portion of the received signal is computed at step 98 in FIG. 6 and a display can be generated at step 100 which displays each pixel in the area of interest in the tissue with a display characteristic representative of the value of slope, amplitude or amplitude uncertainty for the spectrum of the received signal for the time portion that corresponds to the particular spatial sample of the signal. Because of the known variations in these spectral characteristic values for different tissue type, an example of which is illustrated in FIG. 7 and FIG. 8, the display of these characteristics can provide evidence to a physician viewing the display of the possible presence or absence of a particular type of disorder in the tissue being examined.

FIG. 10 is a diagram showing the results of a spectrum analysis of a signal which has been reflected from a subretinal hemorrhage. Curve 134 in FIG. 10 shows a significant degree of variation in amplitude over the spectral region of 5 to 15 MHz. This large variation of spectral amplitude will provide a significantly larger amount of spectral amplitude uncertainty in the amplitude of the zero intercept. This variation can help distinguish this type of tissue disorder from metastatic carcinomas, one of which is illustrated in FIG. 8, and has a relatively small amount of amplitude variation from the linearized curve 126.

Step 96 in FIG. 6 relates to recognition of noise signals in time portions of the received reflected ultrasonic signal. Noise recognition can be used to provide suppression of noise signals in a display, which results in a clearer appearance of the display than would otherwise be obtained. Noise recognition in accordance with the present invention is performed by comparing the characteristics of noise signals, which can be known, to the characteristics of signals which result from tissue reflections.

Figure 9:
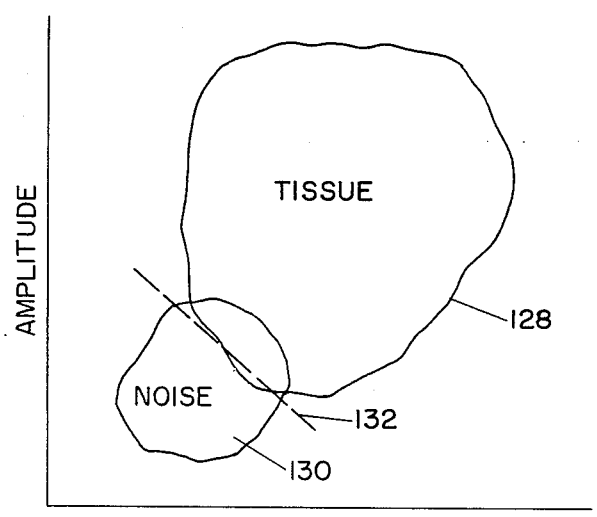
FIG. 9 is a diagram illustrating areas of spectral amplitude and spectral slope which are characteristic of signals reflected from tissue and characteristics of noise signals.

FIG. 9 is an illustration of a mapping of spectral amplitude and spectral slope. The mapping shows that there is a region 128 of amplitude and slope wherein tissue reflections are usually encountered. There is a further region 130 which is characteristic of the spectral characteristic values of spectral amplitude and spectral slope which result from noise type signals. By providing a boundary selected to exclude many of the noise signals 130, such as linear boundary 132, it is possible to identify those portions of those received signal samples which are noise characteristics, and in this case provide a selected fixed display characteristic for the corresponding pixels, such as a totally black portion of the display monitor. Using this technique the display will show only images of signals which are likely to be representative of tissue, and thus many noise type signals, which could otherwise confuse the display image, can be eliminated. Such noise recognition signals are given a selected value for each pixel of the image and can be used to suppress noise signal images in any of the displays in accordance with the present invention. Accordingly a dotted line is provided from the noise recognition step in FIG. 6 to all of the display systems shown. In many cases, the recognition of noise is expedited by also examining the spectral energy at additional frequencies (e.g., 10 MHz) where noise levels are typically lower than tissue signal levels.

Figure 11:
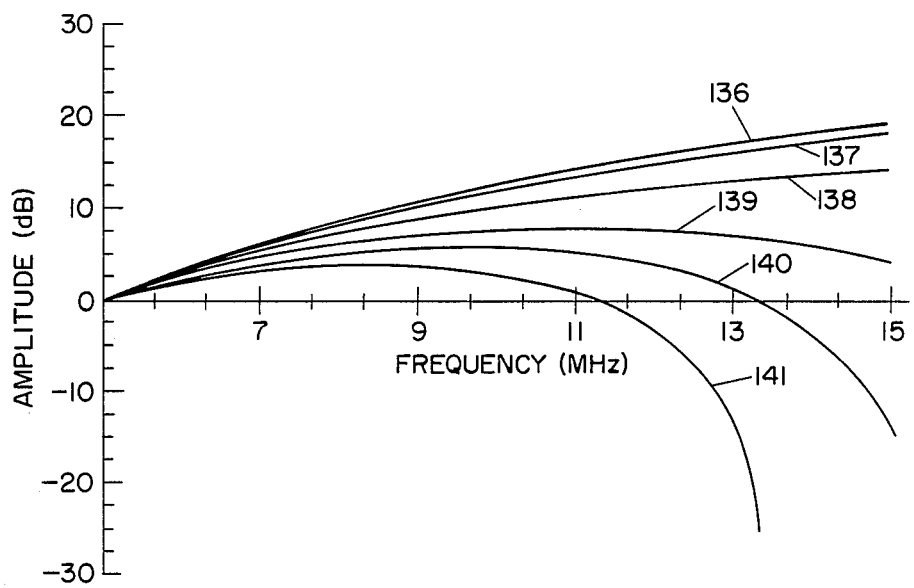
FIG. 11 is a graph of spectral amplitude and is a function of frequency for signals reflected from spheres having various radii.

FIG. 11 shows theoretically predicted spectra for spatially uniform distributions of small spherical particles with different radii. The spectral shapes are influenced in a specific manner depending upon the size of the particles. A linear fit to these spectra shows that spectral slope, in particular, is related to particle size, when the sized fall within a certain range. For more complex scatterers, a spatial auto-correlation width defines the effective scatterer size, and a published report provides the needed equations to determine similar relations between this effective size and spectral slope. Thus, the effective scatterer size can often be estimated on the basis of measured spectral slope.

Figure 12:
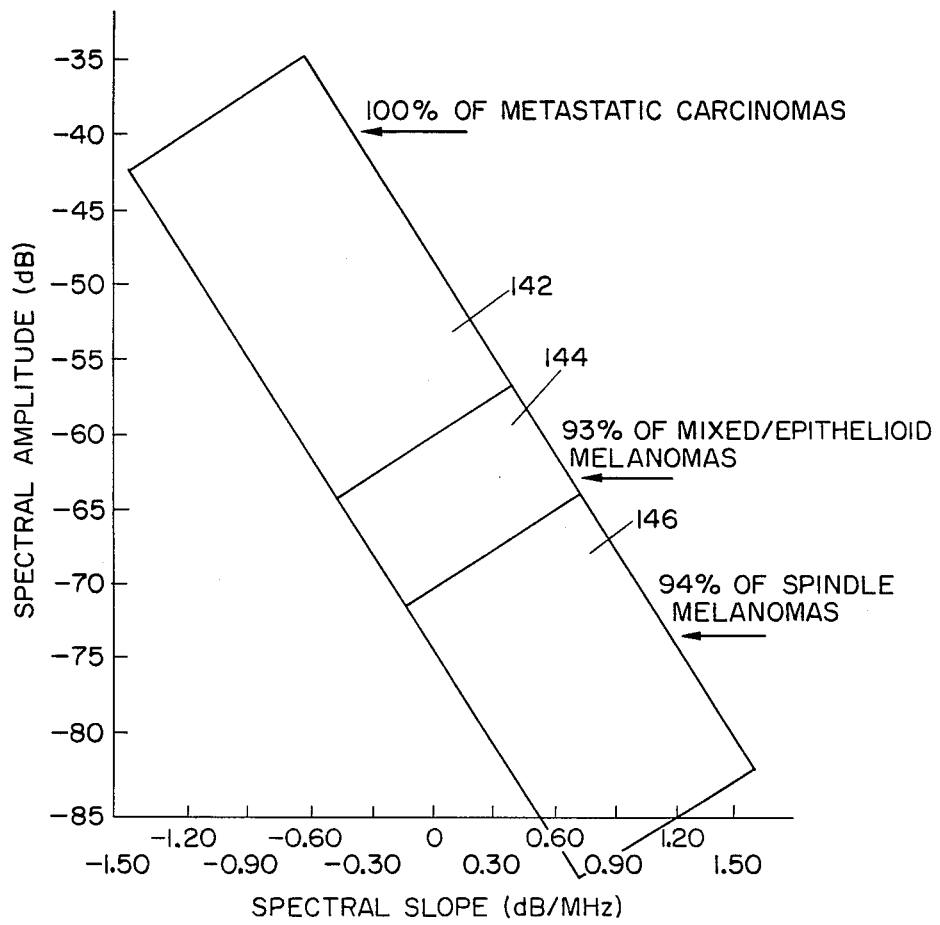
FIG. 12 is a graph of spectral amplitude plotted as a function of spectral slope showing regions which are characteristic of various tissue types.

FIG. 12 is a mapping of spectral amplitude values and spectral slope values for various samples of tissues which have been examined using the apparatus of FIG. 1 and which have been determined to have particular tissue characteristics by reason of subsequent pathological examination following removal of the tissue. Tissues having metastatic carcinoma tissue characteristics generally fall into an area of the FIG. 12 mapping labeled 142. Tissues having mixed/epitheliod melanoma tissue characteristics generally fall into an ares of the mapping 144 and tissues having spindle B melanoma tissue characteristics generally fall into the area 146. Accordingly, comparison of spectral characteristic values of amplitude and slope to the mapping of FIG. 12 can give an indication of tissue type. This comparison can be done in step 110 of FIG. 6 where the values of amplitude and slope, and also possibly spectral amplitude uncertainty, are compared to values for known tissue types in the data bank, and a display can be generated by providing a tissue type correlation signal at step 112 which indicates a particular tissue type, for example, a different color for each different type of tissue.

At step 114 a display is generated which may include display elements having display characteristics selected according to the tissue type correlation signal. Thus pixels of the display which correspond to spatial samples of the tissue which shown an indication of metastatic carcincoma may be displayed in red, tissues which have characteristics of mixed/epitheliod melanomas may be displayed in green and tissues which have tissue spectral characteristics values indicative of spindle B melanomas may be displayed using another color, such as blue.

Because of the availability of the data bank on spectral characteristic values for known tissue types, it is possible, using known computational techniques, to develop discriminant functions which would be helpful in identifying tissue types. The discriminant functions are linear combinations with varying weightings for each of the spectral characteristic values which provide in combination the greatest distinction among tissue types. In the case of three characteristic values of spectral amplitude, spectral slope and spectral amplitude uncertainty, it is possible to generate three independent discriminant functions which would be useful in identifying such tissues. Two such functions can also be used together or a single function can be used.

Figure 13:
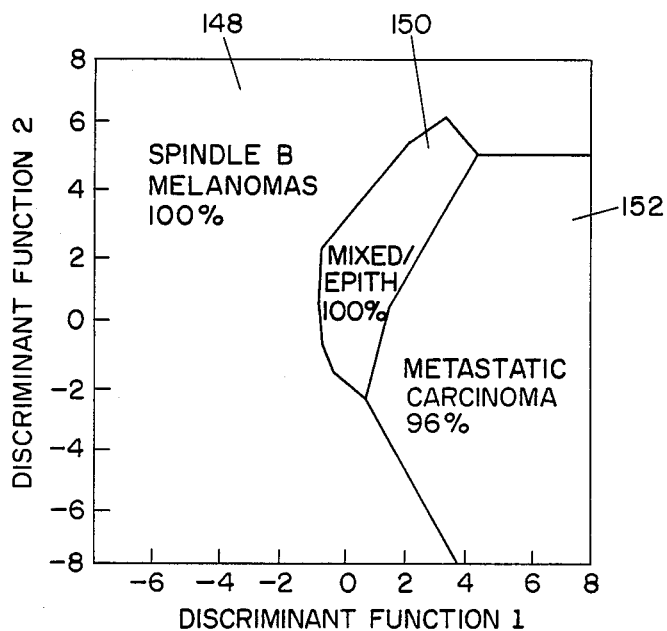
FIG. 13 is a graph showing the areas of two discriminant functions which are representative of various tissue types.

FIG. 13 is an indication of two discriminant functions which were generated using the characteristic values of spectral amplitude, spectral slope and spectral amplitude uncertainty. In the mapping of FIG. 13 the first discriminant function is plotted along one axis and the second discriminant function is plotted along the other axis. The areas of the two discriminant functions which closely correspond to particular tissue types are indicated in the mapping. This use of discriminant functions in conjunction with a data bank of information from known tissue types as indicated in FIG. 13 provides a high correlation of tissue type identification; and can provide a reliable and useful means for identifying tissue type in connection with analysis of received signals.

Figure 14:
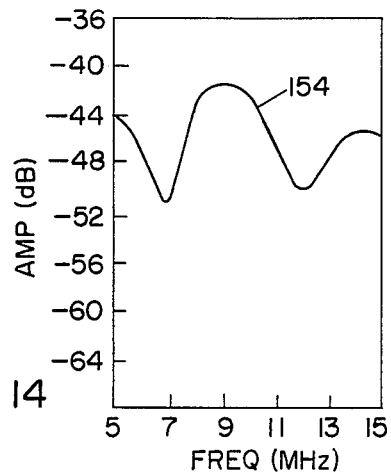
FIG. 14 is a diagram of spectral amplitude as a function of frequency for a detached retina.
Figure 15:
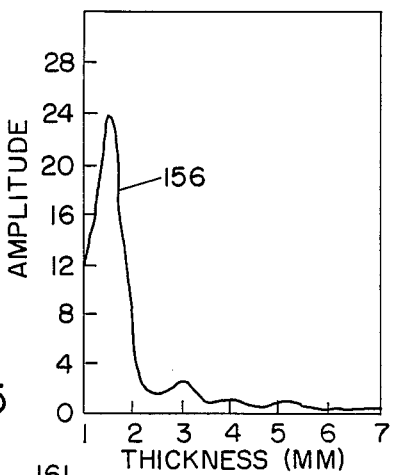
FIG. 15 is a diagram showing cepstrum amplitude as a function of thickness for the tissue which has the spectrum of FIG. 14.

FIG. 14 shows a plot of the amplitude (expressed in dB) of the power spectrum versus frequency for a case of a detached retina. It can be seen that the curve 154 represents a fairly periodic function. Such periodicities are related to the thickness or periodic spacings of well defined structures within the examined tissue region. FIG. 15 is a plot of cepstral amplitude versus thickness which is obtained by taking the Fourier transform of the line 154 of FIG. 14. This line 156 indicates that the scanned material has a marked thickness of about 0.15 millimeters.

Cepstral results are similar to those of spatial correlation functions that often may be computed by taking the Fourier transform of a power spectrum expressed in linear amplitude units rather than in dB, or may be computed directly from RF signals. As is well-known, both cepstral and correlation functions provide periodicity data descriptive of the dimensions and spacings of spectral tissue elements.

Figure 16:
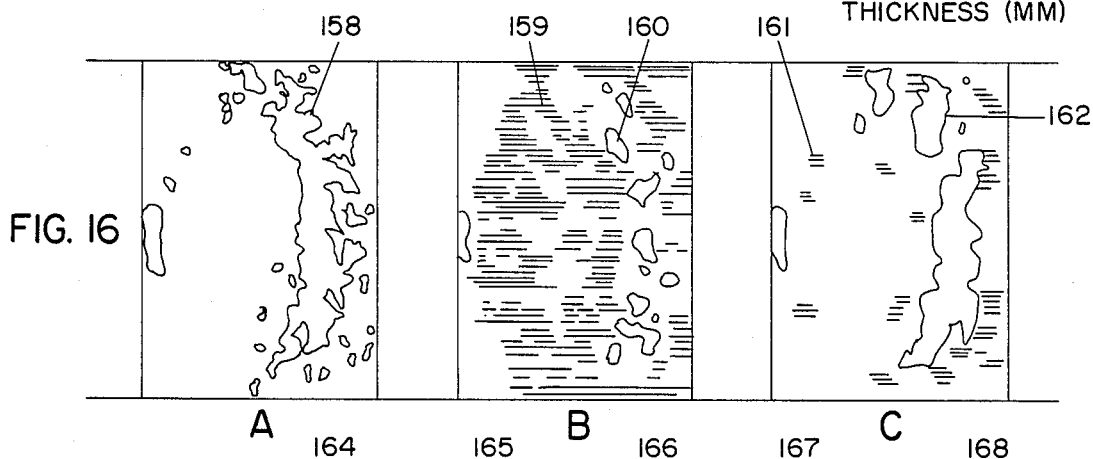
FIG. 16 shows displays of a tissue region with a malignant melanoma FIG. 16A showing a B-scan image.
Figure 17:
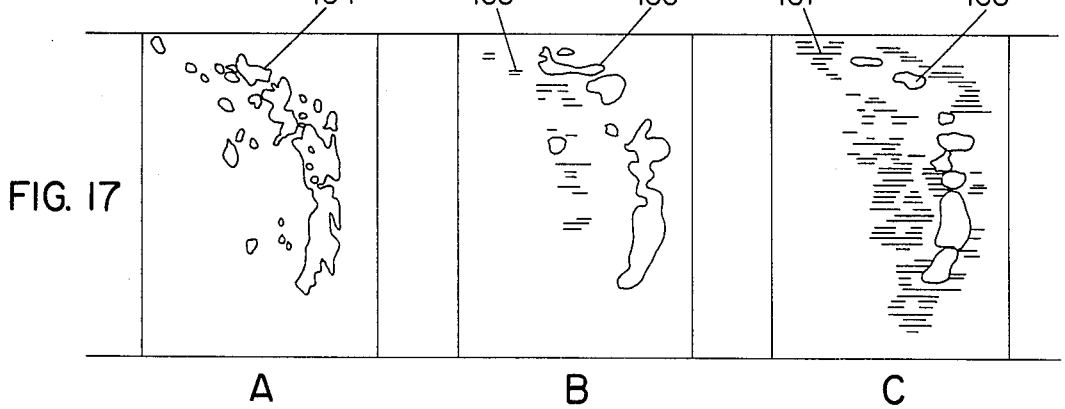
FIG. 17 is an illustration of displays of a cross section of a tissue region having a metastatic carcinoma.

FIGS. 16 and 17 show the effects of straining a particular image obtained from ultrasonic scanning and its effectiveness as an aid to identifying a particular disease. FIG. 16*a* shows a standard gray scale (unstained) image of an eye having a malignant melanoma. Numeral 158 identifies the image before staining. FIG. 16*b* shows the image of 16*a* stained to highlight those tissue segments having malignant melanoma characteristics. Regions 159 are the stained portions of the image, whereas regions 160 are the unstained portions. FIG. 16*b* contains significant areas of staining 159, consistent with an identification of the disease as malignant melanoma. FIG. 16*c* shows the tissue of FIG. 16*a* stained to highlight those tissue segments having another type of disease, namely, metastatic carcinoma, with regions 161 being the stained portions and regions 162 being the unstained portions. It will be seen that the stained regions 161 are fairly small and few in number, thereby being consistent with a diagnosis that the examined tissue region does not contain metastatic carcinoma.

FIG. 17 is similar to FIG. 16 in that it shows a standard gray scale image in FIG. 17*a*, staining for one type of disease in 17*b*, and staining for a second type of disease in 17*c*. FIG. 17*b* shows staining for malignant melanoma, and since the regions of staining 165 are relatively few and small, and the unstained portions 166 are relatively large, is consistent with a diagnosis that the tissue region does not contain malignant melanoma. On the other hand, FIG. 17*c*, which is stained for metastatic carcinoma, shows a large number of stained regions 167, thereby being consistent with a diagnosis that the tissue is a metastatic carcinoma.

A clinically important use of the preceeding methods according to the invention is in monitoring the growth of suspected disease and the response of treated tissues to therapeutic modalities. For example a malignant melanoma may be treated by various forms of radiation and changes induced thereby within the tumor will cause corresponding changes in measured spectral values. Thus the internal response to these tumors to this treatment can be monitored by repeating these methods at various times.

Figure 18:
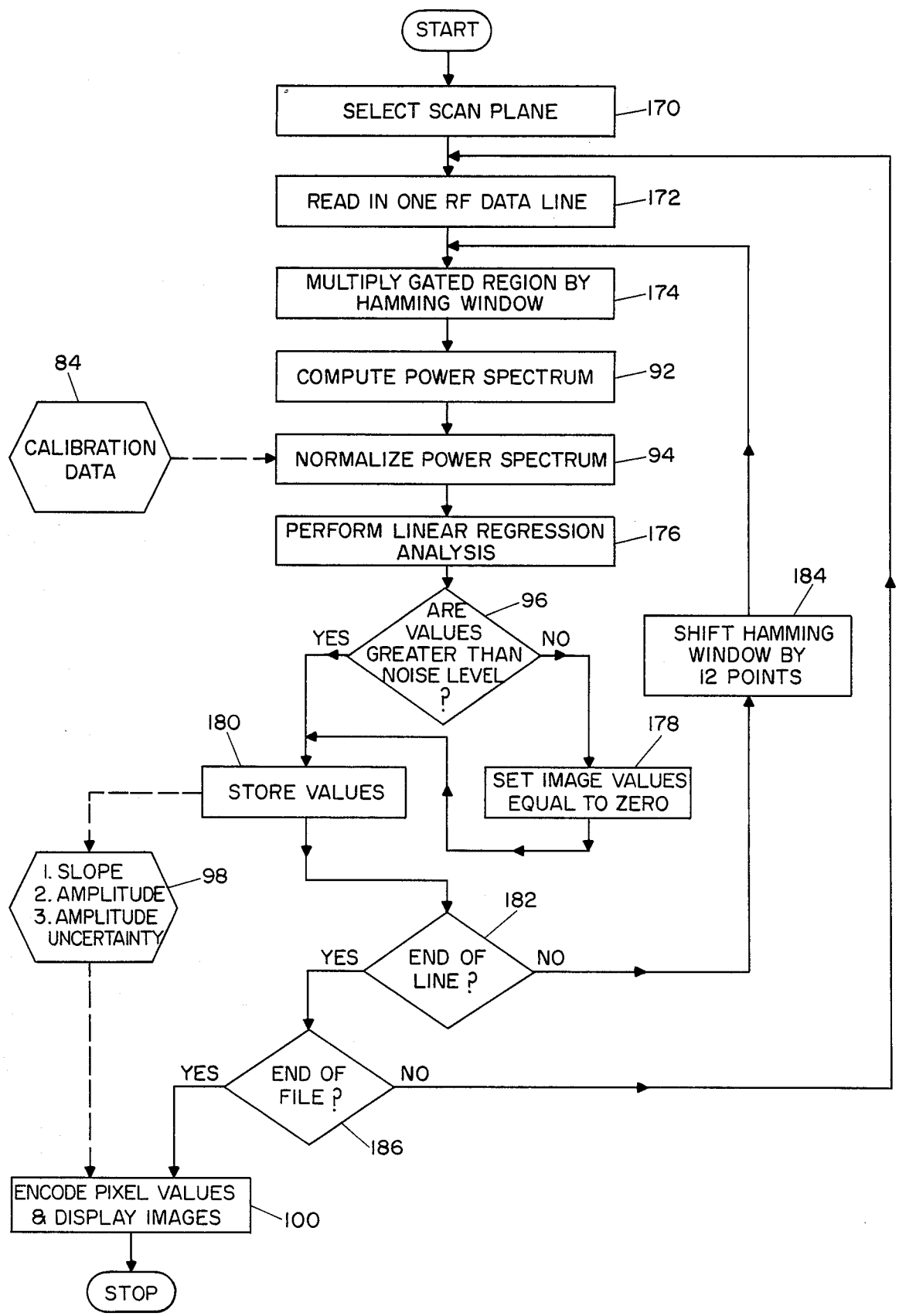
FIG. 18 is a program flow diagram showing the details for spectral characteristic value imaging.

FIG. 18 is a program flow diagram showing the details for the spectral characteristic value imaging in which image displays are produced of such spectral features as amplitude, slope and amplitude uncertainty. In the first step 170, the operator selects a particular scan plane desired to be examined. In step 172, one line of RF data is read into local memory for processing. The gated region is multiplied by the Hamming window in step 174, and then the power spectrum is computed in step 92 and normalized in step 94 with the aid of calibration data 84. A linear curve fitting is performed in step 176 by linear regression analysis.

Since the processed data are to be displayed, noise recognition and suppression are performed in steps 96 and 178. The values of slope, amplitude and amplitude uncertainty are then stored in step 180 for that particular pixel. At step 182, the program checks to see whether the last pixel for that line has been reached. If it has not been reached, the Hamming window is shifted by 12 points (12 points of RF data representing 1 pixel) in step 184, and the program goes to step 174 and repeats the process as indicated, until all of the pixels in a particular RF data line have been processed, whereupon in step 186, the program determines whether the end of the file has been reached, indicating processing of all of the RF data lines. If data lines are yet to be processed, the program returns to step 172 and repeats the loop of steps until all of the RF data lines have been processed. Once all of the data lines have been processed, the pixel values are encoded and image is displayed in step 100 and the program then stops. The displayed image values are encoded to represent, in gray scale or color, the value of the spectral parameter being imaged. In addition, specific colors can be used to depict those values falling within the ranges exhibited by specific diseases.

Figure 19:
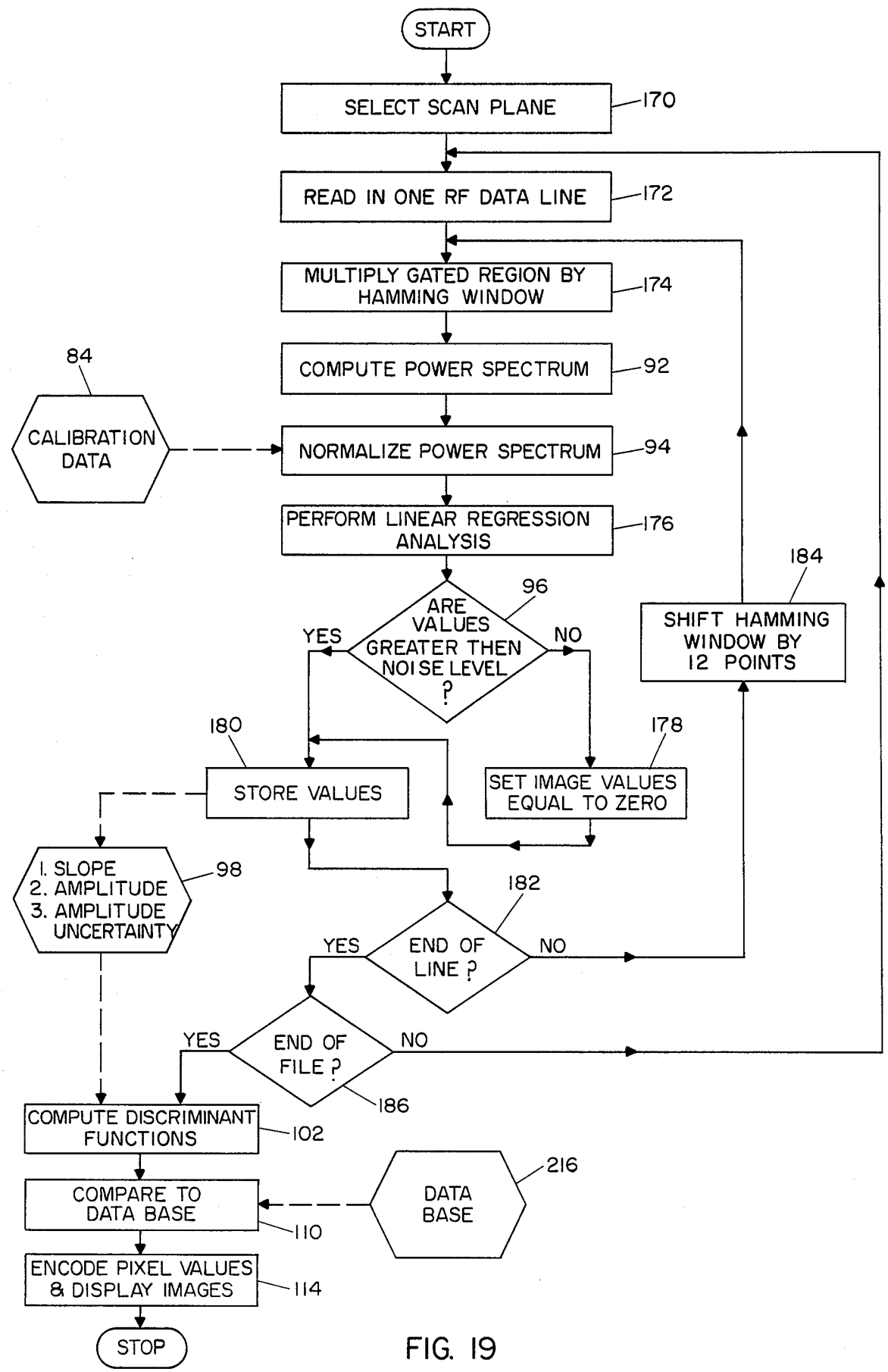
FIG. 19 is a program flow diagram showing the details of a program for generating images with tissue characteristic staining.

FIG. 19 is a program flow diagram showing the details of a program for generating images having tissue characteristic staining. Many of the steps of this program are substantially identical to the program illustrated in FIG. 18. The principal difference is the addition of step 102 wherein the disriminant functions are computed and in step 110 wherein the computed data are compared to the data base which is stored in the memory of the computer at 216. A display of the stained image is then made at step 114, the displayed images are encoded to represent in gray scale or color the type of tissue consistent with the discriminant function value obtained or computed for each pixel.

Figure 20:
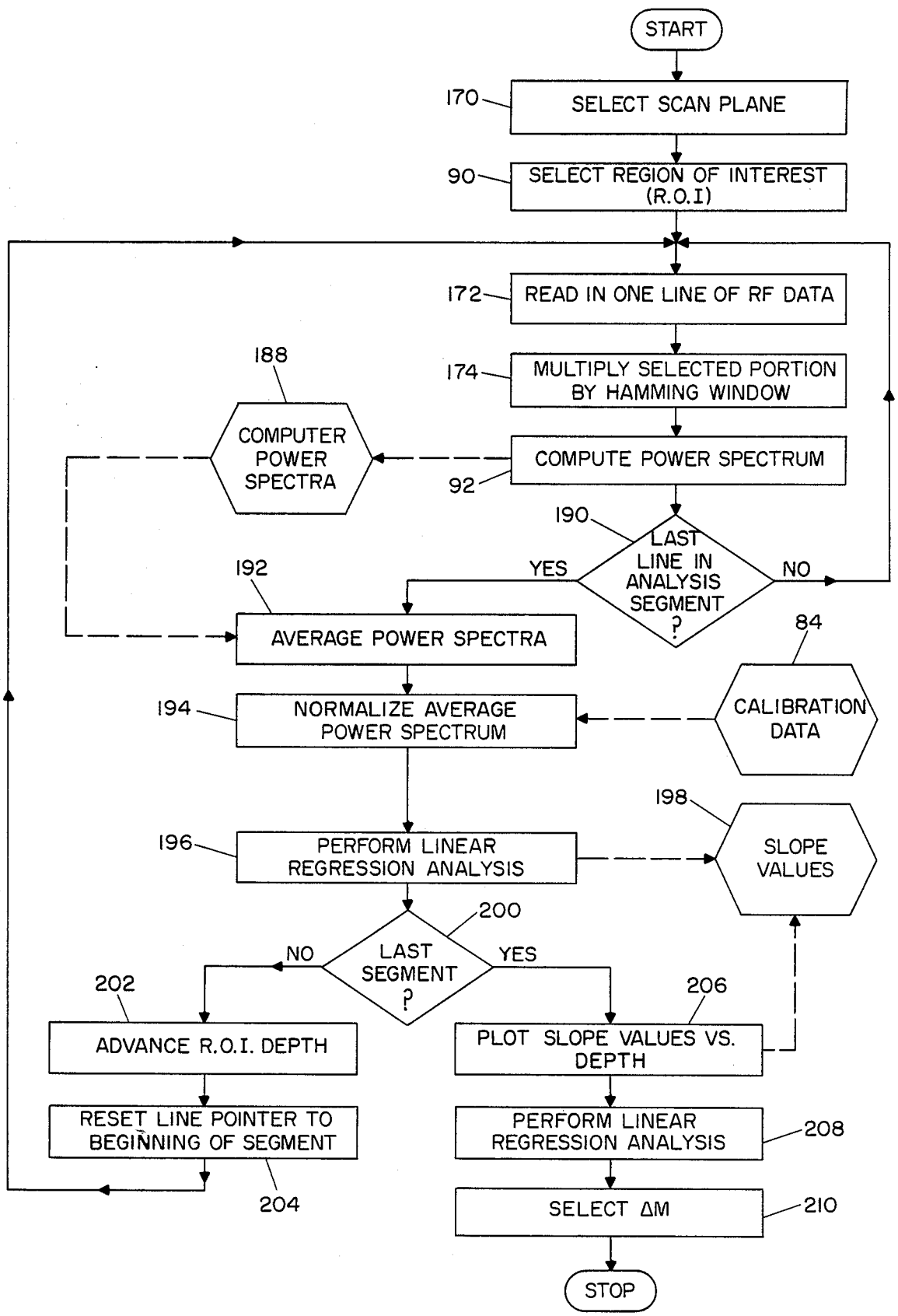
FIG. 20 is a program flow diagram for tissue characterization by measuring the deviation from uniform spectral slope variation with distance.
Figure 23:
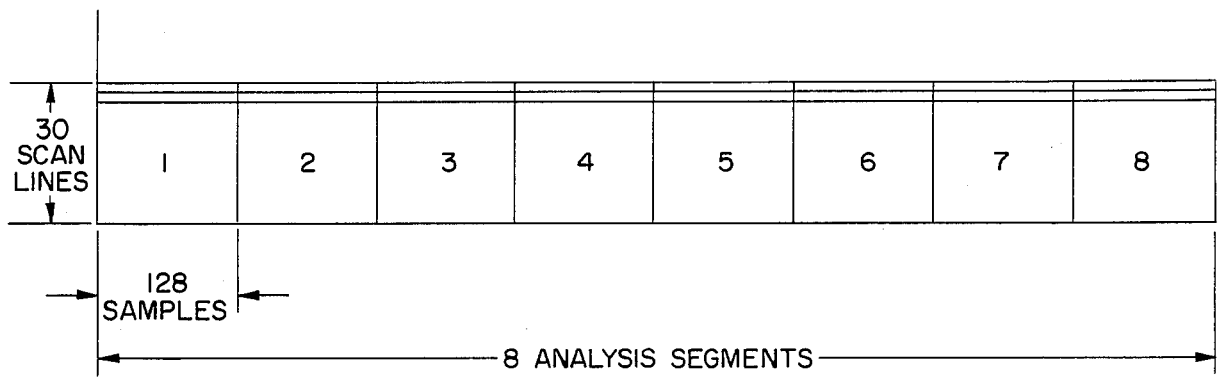
FIG. 23 is a diagram of sections of tissue used in a spectral slope deviation analysis.
Figure 24:
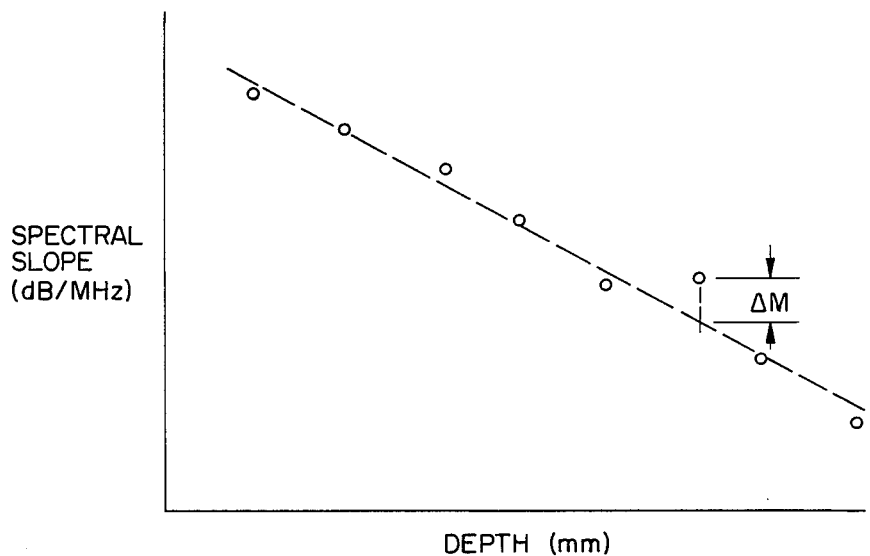
FIG. 24 is a diagram illustrating a linearized plot of spectral slope as a function of tissue depth, with an illustration of spectral deviation determination.

FIG. 20 is a program flow diagram for tissue characterization by deviation from uniform spectral slope variation with respect to distance, and will be described in conjunction with FIGS. 23 and 24. The first step 170 in FIG. 20 is for the operator or physician to select the desired scan plane. The desired region of interest (ROI) is then selected in step 90. The selected region of interest is shown in FIG. 23 and comprises eight analysis segments each of which is 30 scan lines and 128 digital samples across. One line of RF data is read in at step 172 and this data is multipled by the Hamming window in step 174. The power spectrum is computed at 92 and this data is written to the computer disk at step 188. The program also determines whether the last line in the analysis segment has been evaluated, and if not, a subsequent line of RF data in that analysis segment is read in at step 172 and this loop is repeated.

Once the last line in the particular analysis segment has been read in, the average power spectrum is computed in step 192 using the computed power spectra from block 188. The average power spectrum is normalized at step 194 using calibration data previously stored at block 84. A linear curve fitting is performed at step 196 using linear regression analysis, and the result, including a slope value, is written to disk at step 198. The program also determines whether the last segment (the eighth analysis segment as shown in FIG. 23) has been analyzed. If it has not, the region of interest depth is advanced in block 202, and a line pointer is reset to the beginning of the next segment in block 204, whereupon the program returns to step 172 to repeat this and subsequent steps. Once the last segment has been reached, the values of spectral slope are plotted versus depth in block 206, as shown in FIG. 24. It will be seen that one point is plotted for each of the eight analysis segments. In step 208, a linear curve fit is obtained as indicated by the dotted line in FIG. 24. The downward slope in the line in FIG. 24 is due to the fact that the ultrasonic signals become weaker or attenuated because of their further penetration into the tissue, and higher frequencies are attenuated more strongly than lower frequencies. If characteristics of the tissue vary among segments there will be departures from the straight line fit. One means of evaluating this variation is by computing $\Delta M$, which is the maximum positive deviation of spectral slope from the linear function. This is determined in step 210, which, for the data shown in FIG. 24, is the distance between the value of the spectral slope for the sixth analysis segment and the linear curve fitted to this data. The value of $\Delta M$ is then used, alone or in conjunction with other parameters, to perform a tissue diagnosis.

Figure 21:
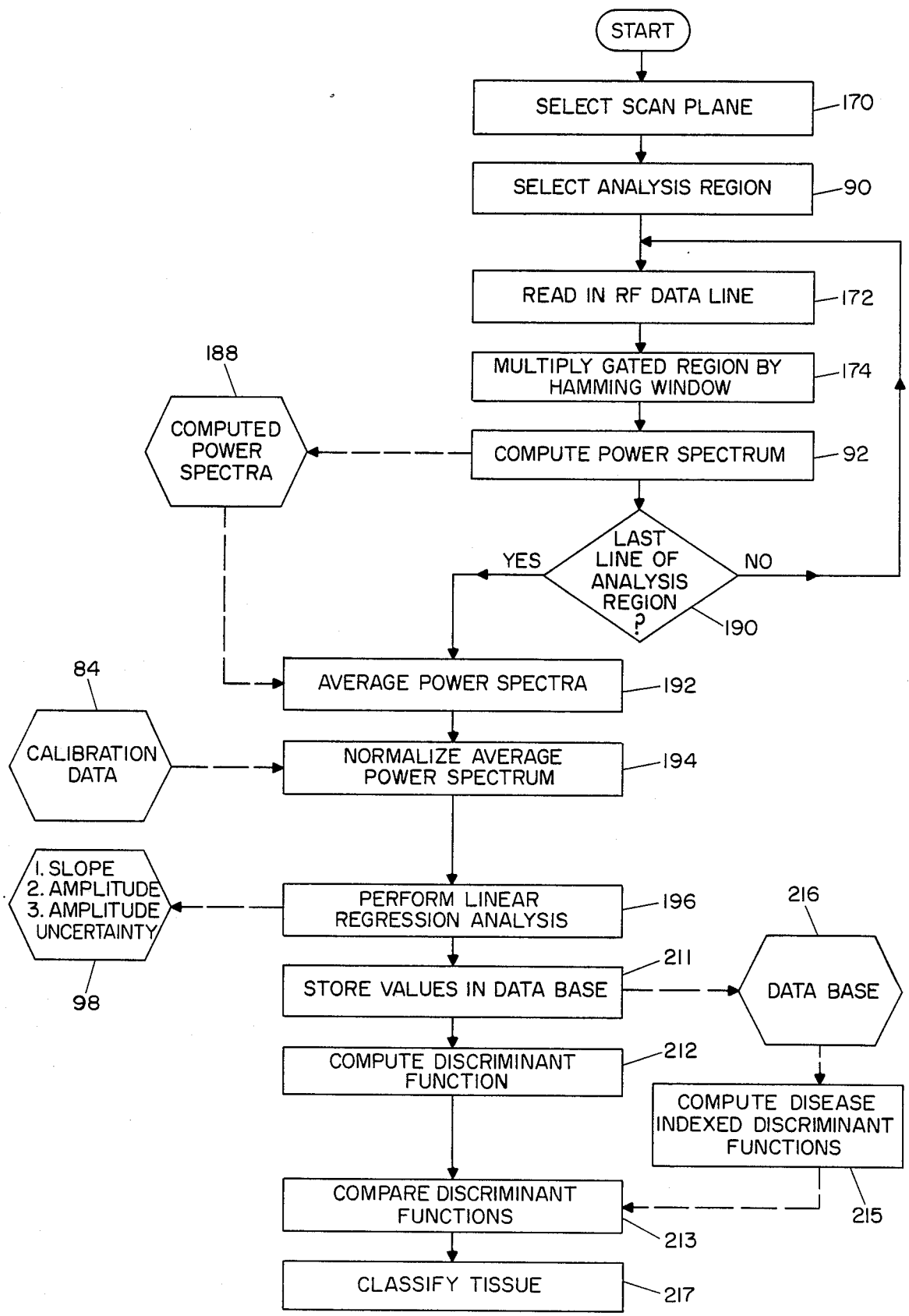
FIG. 21 is a program flow diagram for tissue characterization using a discriminant function.

FIG. 21 is a program flow diagram for tissue characterization using a discriminant function. Several of the initial steps in this program are substantially similar to steps in FIGS. 18 and 19. However, an additional initial step 90 is included wherein the analysis region is selected by the operator or physician. After step 92, wherein the power spectrum is computed, the power spectra are written to disk at 188, and the program also determines whether the last line in the analysis region has been reached in step 190. If the last line has not bee reached, subsequent RF data lines are read in at step 172. When the last line of the analysis region has been reached, the average power spectrum is computed at step 192 and then the average power spectrum is normalized at step 194 using calibration data from block 84. Linear curve fitting is performed by linear regression analysis techniques at step 196, and the result in slope, amplitude and amplitude uncertainty data is written to the computer disk at step 98. In step 211 these values are also stored in the data base 216. The discriminant functions are computed at step 212 using the slope, amplitude and amplitude uncertainty data previously computed, and at step 213 the results of such computations are compared to the disease indexed discriminant functions compiled at step 215. The tissue is then classified by type at step 217.

Figure 22:
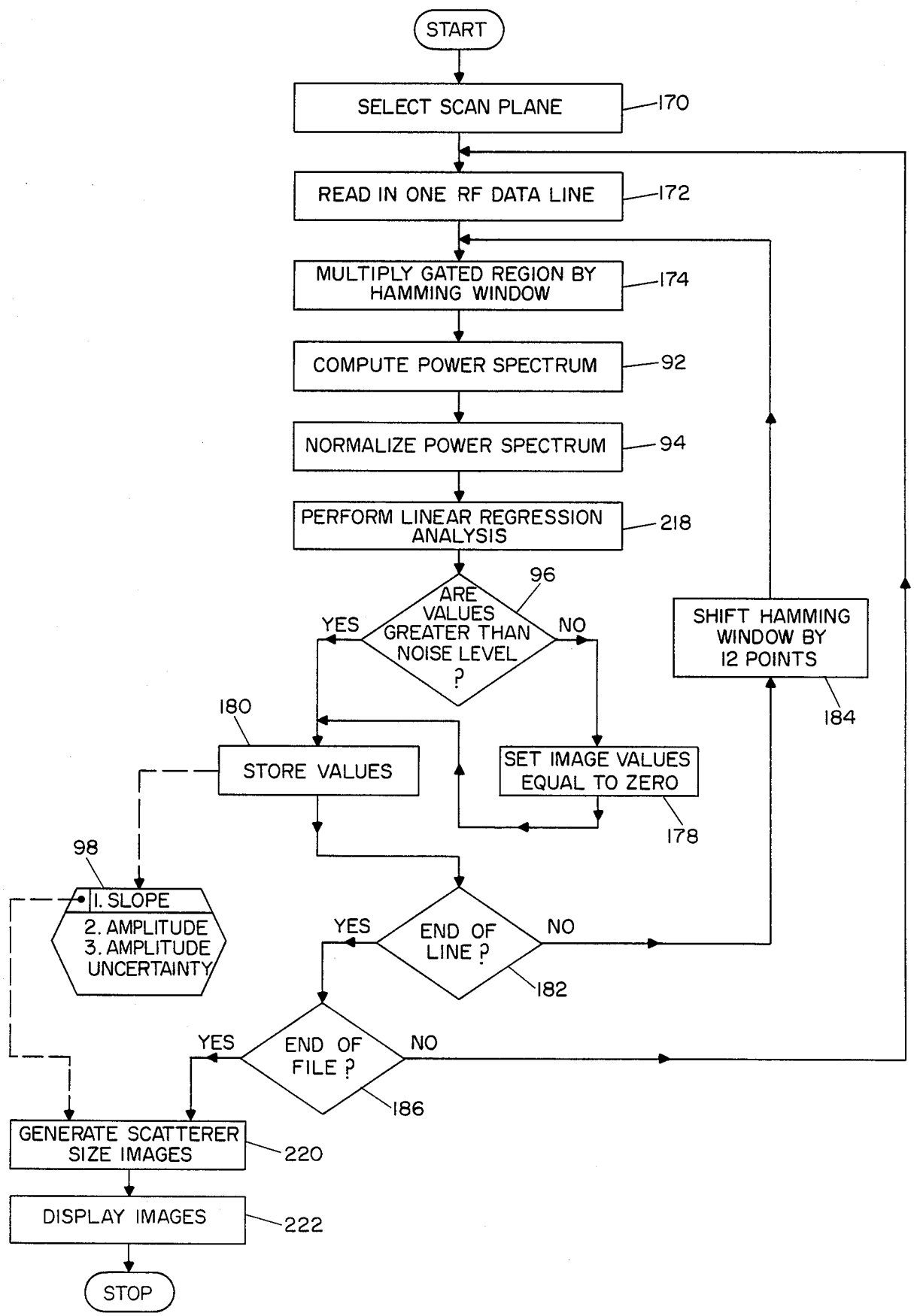
FIG. 22 is a program flow diagram for imaging according to scatterer size.

FIG. 22 is a program flow diagram for imaging according to effective scatterer size. This program is substantially the same as the programs in FIGS. 18 and 19, except that at the end in step 220, scatterer size images are generated, and in block 222 these images are displayed after being encoded in gray scale or color to indicate scatterer size.

From the foregoing, it will be observed that numerous variations and modifications may be effected without departing from the true spirit and scope of the novel concept of the invention. It is to be understood that no limitation with respect to the specific embodiment or methods illustrated herein is intended or should be inferred. For example, the transmitted acoustic signals need not be wideband signals, nor need they be pulses. Further the frequency of the transmitted need not be limited to the ultrasonic range. Further the methods according to the invention may be employed to bodies of material other than the human body. Further, any of the formed images may be improved by signal processing techniques, including spatial filtering to reduce statistical fluctuations of spectral data, and these techniques may be used prior to or following the encoding of display characteristics. It is, of course, intended to cover by the appended claims all such modifications as fall within the scope of the claims.

We claim:

1. A method for processing reflected acoustic signals from a body of material and for generating a display of at least a portion of said body, representative of characteristics of said material comprising:
   transmitting acoustic signals into a region of interest in said body in an ordered spatial progression;
   receiving reflected acoustic signals from said body;
   analyzing the frequency content of selected time portions of said received signal to derive spectral data representative of spectral power as a function of frequency for spatial samples of said body within said body region of interest; said spatial samples corresponding to said time portions of said received signal;

normalizing said spectral data to values of said spectral data for an object with known reflection characteristics;

deriving spectral characteristic values from said normalized spectral data independently for each of said spatial samples, said spectral characteristic values being selected from the group comprising frequency specific normalized spectral amplitude, spectral slope and spectral amplitude uncertainty; and generating a display of said body region of interest with a display characteristic for each of said spatial samples selected in accordance with said derived spectral characteristic values.

2. A method as specified in claim 1 wherein said step of deriving spectral characteristic values comprises deriving a value representative of frequency specific normalized spectral amplitude for each of said samples.

3. A method as specified in claim 1 wherein said step of deriving spectral characteristic values comprises deriving a value representative of spectral slope for each of said samples.

4. A method as specified in claim 1 wherein said step of deriving spectral characteristic values comprises deriving a value representative of spectral amplitude uncertainty for each of said samples.

5. A method as specified in claim 1 wherein said step of deriving spectral characteristic values comprise deriving at least two of said spectral characteristic values; and deriving combined spectral characteristic values from said at least two sets of spectral characteristic values, said combined spectral characteristic values being derived to correlate with significant material characteristics; and wherein said step of generating a display comprises generating a display characteristic for each spatial sample in accordance with said derived combined spectral characteristic values.

6. A method as specified in claim 5 wherein said step of deriving spectral characteristic values comprises deriving at least three sets of said spectral characteristic values and deriving said combined spectral characteristic values from said three sets.

7. A method as specified in claim 1 wherein said step of generating a display comprises generating a display for each spatial region with a color selected in accordance with said derived spectral characteristic value.

8. A method for processing reflected acoustic signals from a body of material and for generating a display of at least a portion of a cross-section of said body, representative of characteristics of said material, comprising:

transmitting acoustic signals into a region of interest in said body in an ordered spatial progression corresponding to said cross-section;

receiving reflected acoustic signals from said body, said signals comprising signal time intervals corresponding to reflections from successive linear acoustic paths through said material in said spatial progression;

dividing selected time periods of said received signals into signal time portions, each signal time portion comprising a selected time sample of one of said signal time intervals and corresponding to a spatial sample of said material along one of said acoustic paths in said region of interest;

performing a spectral analysis of each of said signal time portions to derive therefrom spectral data representative of the spectral power level of said signal time portion at various frequencies within the frequency band of said acoustic pulse signals;

normalizing said spectral data to values of said spectral data for an object with known reflection characteristics;

deriving at least one spectral characteristic value from said normalized spectral data independently for each of said signal time portions corresponding to a segment of an acoustic path in a region of interest of said cross-section, said spectral characteristic value being selected from the group consisting of frequency specific normalized spectral amplitude, spectral slope and spectral amplitude uncertainty;

and generating a display of said region of interest of said cross-section, said display having elemental display areas corresponding to said spatial samples, each of said display areas having a display characteristic representative of said spectral characteristic value.

9. A method for processing reflected acoustic signals from body tissue and for generating a display of at least a portion of said tissue, representative of clinicaly significant characteristics of said tissue comprising:

transmitting ultrasonic signals into a region of interest of said tissue in an ordered spatial progression;

receiving reflected ultrasonic signals from said tissue;

performing a spectral analysis of selected time portions of said received signal to derive spectral data representative of spectral power as a function of frequency for spatial samples of said tissue within said region of interest, said spatial samples corresponding to said time portions of said received signal;

normalizing said spectral data to values of said spectral data for an object with known reflection characteristics;

deriving spectral characteristic values from said normalized spectral data independently for each of said spatial samples, said spectral characteristic values being selected from the group comprising frequency specific normalized spectral amplitude, spectral slope and spectral amplitude uncertainty; and generating a display of said tissue regionof interest with a display characteristic for each of said spatial samples selected in accordance with said derived spectral characteristic values.

10. A method as specified in claim 9 wherein said step of deriving spectral characteristic values comprises deriving a value representative of frequency specific normalized spectral amplitude for each of said samples.

11. A method as specified in claim 9 wherein said step of deriving spectral characteristic values comprises deriving a value representative of spectral slope for each of said samples.

12. A method as specified in claim 9 wherein said step of deriving spectral characteristic values comprises deriving a value representative of spectral amplitude uncertainty for each of said samples.

13. A method as specified in claim 9 wherein said step of deriving spectral characteristic values comprises deriving at least two spectral characteristic values selected from said group; and deriving combined spectral characteristic values from said at least two sets of spectral characteristic values, said combined spectral characteristic values being derived to correlate with clinically significant tissue characteristics; and wherein said step of generating a display comprises generating a display characteristic for each spatial sample in accordance with said derived combined spectral characteristic values.

14. A method as specified in claim 13 wherein said step of deriving spectral characteristic values comprises deriving at least three sets of spectral characteristic values and deriving said combined spectral characteristic values from said three sets.

15. A method as specified in claim 16 wherein said step of generating a display comprises generating a display for each spatial region with a color selected in accordance with said derived spectral characteristic value.

16. A method for processing reflected ultrasonic signals from body tissue and for generating a display of at least a portion of a cross-section of said tissue, representative of clinically significant tissue characteristics, comprising:

transmitting wideband ultrasonic pulse signals into a region of interest of said tissue in an ordered spatial progression corresponding to said cross-section;
 receiving reflected ultrasonic signals from said tissue, said signals comprising signal time intervals corresponding to reflections from successive linear acoustic paths through said tissue in said spatial progression;
 dividing selected time periods of said received signals into signal time portions, each signal time portion comprising a selected time sample of one of said signal time intervals and corresponding to a spatial sample of said tissue along a segment of one of said acoustic paths in said region of interest;
 performing a spectral analysis of each of said signal time portions to derive therefrom spectral data representative of the power level of said signal time portion at various frequencies with the frequency band of said ultrasonic pulse signals;
 normalizing said spectral data to values of spectral data for an object with known reflection characteristics;
 deriving spectral characteristic values from said normalized spectral data independently for each of said signal time portions corresponding to a segment of an acoustic path in a region of interest of said cross-section, said spectral characteristic value being selected from the group consisting of frequency specific normalized spectral amplitude, spectral slope and spectral amplitude uncertainty;
 and generating a display of said region of interest of said cross-section, said display having elemental display areas corresponding to said spatial samples, each of said display areas having a display characteristic representative of said spectral characteristic value.

17. A method for generating a display at least a portion of a cross-section of eye tissue representative of the presence in said cross-section of at least one known tissue type, comprising:

transmitting ultrasonic signals into said eye tissue in an ordered spatial progression of acoustic paths corresponding to said cross-section;
 receiving reflected ultrasonic signals from said tissue comprising signal time intervals corresponding to reflections from said acoustic paths through said tissue;
 dividing selected time periods of said received signals into signal time portions, each signal time portion comprising a selected time sample of one of said signal time intervals and corresponding to a spatial sample of said tissue along a segment of one of said acoustic paths in a region of interest of said eye tissue;
 performing a spectral analysis of each of said signal time portions to derive therefrom spectral data representative of the power level of said signal time portions at various frequencies within the frequency band of interest of said ultrasonic pulse signals;
 normalizing said spectral data to values of said spectral data for an object with known reflection characteristics;
 deriving spectral characteristic values from said normalized spectral data independently for each of said signal time portions corresponding to a segment of an acoustic path in a region of interest in said cross-section, said spectral characteristic value being selected from the group consisting of frequency specific normalized spectral amplitude, spectral slope and spectral amplitude uncertainty, said selection being made to correspond with distinguishing properties of aaid known tissue types;
 and generating a display of said region of interest of said cross-section, said display having elemental display areas corresponding to said spatial sample, each of said display areas having a spectral characteristic value corresponding to said known tissue type being provided with a distinguishing display characteristic;
 whereby a predominance of said distinguishing display characteristic in a portion of said display is indicative of the presence of said known tissue type.

18. A method for processing reflected acoustic signals from a body of material and for generating a display of at least a portion of said body, representative of characteristics of said material comprising:

transmitting acoustic signals into a region of interest in said body in an ordered spatial progression;
 receiving reflected acoustic signals from said body;
 performing a spectral analysis of selected time portions of said received signal to derive spectral data representative of received signal characteristics for spatial samples of said body within said body region of interest, said spatial samples corresponding to said time portions of said received signal;
 normalizing said spectral data to values of spectral data for a object with known reflection characteristics;
 deriving periodicity data from said normalized spectral data for each of said spatial samples;
 deriving periodicity characteristic values from said periodicity data, said periodicity values being selected to correlate with significant characteristics of said material; and
 generating a display of said body region of interest with a display characteristic for each spatial sample of said region selected in accordance with said derived periodicity characteristic values.

19. A method as specified in claim 18 wherein said step of deriving periodicity data comprises deriving cepstral data.

20. A method as specified in claim 18 wherein said step of deriving periodicity data comprises deriving spatial correlation function data.

21. A method as specified in claim 18 wherein said step of deriving periodicity characteristic values comprises deriving a value representative of effective scattering particle spacing for each of said samples.

22. A method for processing reflected ultrasonic signals from body tissue material and for generating a display of at least a portion of said tissue, representative of average particle size of said tissue comprising:
  transmitting ultrasonic signals into a region of interest of said tissue in an ordered spatial progression;
  receiving reflected ultrasonic signals from said tissue;
  performing a spectral analysis of selected time portions of said received signal to derive spectral data representative of received signal characteristics for spatial samples of said tissue within said region of interest, said spatial samples corresponding to said time portions of said received signal;
  normalizing said spectral data to values of spectral data for an object with known reflection characteristics;
  deriving periodicity data from said normalized spectral data for each of said spatial samples;
  deriving periodicity characteristic values from said periodicity data, said periodicity values being selected to correlate with average particle size of said tissue; and
  generating a display of said body region of interest with a displaycharacteristic for each spatial sample of said region selected in accordance with said derived periodicity characteristic values.

23. A method a specified in claim 22 wherein said step of deriving periodicity data comprises deriving cepstral data.

24. A method as specified in claim 22 wherein said step of deriving periodicity data comprises deriving spatial correlation function data.

25. A method for processing reflected ultrasonic signals from body tissue and for generating a display of said tissue representative of clinically significant tisue characteristic, comprising:
  transmitting ultrasonic signals into said tissue in an ordered spatial progression;
  receiving reflected ultrasonic signals from said tissue;
  performing a spectral analysis of selected time interval portions of said received signal corresponding to spatial samples of said tissue to derive spectral data representative of spectral power as a function of frequency for each spatial sample of said tissue within a tissue region of interest;
  normalizing said spectral data to values of said spectral data for an object with known reflection characteristics;
  deriving spectral characteristic values from said normalized spectral data independently for each of said spatial samples, said spectral characteristic values being selected from the group comprising frequency specific normalized spectral amplitude, spectral slope and spectral amplitude uncertainty;
  generating correlation values for each spatial sample by comparing said spectral characteristic values to corresponding values for tissue having known tissue characteristics; and
  generating a display of said tissue region representative of said correlation values for each spatial sample.

26. A method as specified in claim 25 wherein said step of deriving spectral characteristic values comprises deriving values representative of spectral amplitude.

27. A method as specified in claim 25 wherein said step of deriving spectral characteristic values comprises deriving values representative of spectral slope.

28. A method as specified in claim 25 wherein said step of deriving spectral characteristic values comprises deriving values representative of spectral amplitude uncertainty.

29. A method as specified in claim 25 wherein said step of deriving spectral characteristic values comprises deriving at least two sets of spectral characteristic values selected from said groups, and deriving combined spectral characteristic values from said at least two sets of spectral characteristic values, said combined spectral characteristic values being derived to correlate with clinically significant tissue characteristics.

30. A method as specified in claim 29 wherein said step of deriving spectral characteristic values comprises deriving at least three sets of characteristic values and deriving said combined spectral characteristic values from said three sets.

31. A method as specified in claim 25 wherein said step of generating a display comprises generating a display for each spatial region with a color selected in accordance with said correlation values.

32. A method for analyzing tissue characteristics comprising:
  transmitting ultrasonic signals into said tissue;
  receiving reflected ultrasonic signals from said tissue;
  dividing said received signals into signal time periods representative of ultrasonic signals reflected from regions of increasing depthin said tissue;
  analyzing said received signals for each of said signal time periods to derive spectral data representative of the spectral characteristics for each of said signal time periods;
  normalizing said spectral data to values of said spectral data for an object with known reflection characteristics;
  analyzing said normalizing spectral data to derive values representative of spectral slope for each of said signal time periods;
  analyzing said spectral slope values to define a linear function representative of the variation in spectral slope as a function of depth in said tissue; and
  determining the maximum positive deviation of said spectral slope values from said linear function.

33. A method as specified in claim 32 wherein said ultrasonic signals are transmitted to and received from a plurality of adjacent signal paths, and wherein said step of analyzing said received signals includes analyzing signals from a plurality of said paths to derive average spectral values for said paths.

34. In a system for transmitting ultrasonic signals into material and receiving reflected signals for generating a display representative of signal reflecting characteristics of portions of said material, a method for suppressing noise induced images in said display, comprising:
  dividing said received signal into time sequential signal samples;
  performing a spectral analysis of said signal samples to derive spectral data representative of received spectral characteristics of said samples;
  normalizing said spectral data to values of said spectral data for an object with known reflection characteristics;

analyzing said normalized spectral data to derive values of frequency specific normalized spectral amplitudes at various frequencies and spectral slope for each of said samples;

comparing said values of spectral amplitudes and spectral slope to values characteristics of noise and generating a noise representative signal for signal samples having values within a selected range of said noise characteristic values; and displaying a fixed, selected image in portions of said display corresponding to said signal samples.

35. A method of identifying a tissue type within a region of intrest of body tissue, comprising:

transmitting ultrasonic signals into said tissue;

receiving reflected ultrasonic signals from said region of interest of said tissue;

performing a spectral analysis on said received signal to derive spectral data;

normalizing said spectral data to values of said spectral data for an object with known reflection characteristics;

analyzing said normalized spectral data to derive at least two spectral characteristic values, said values being selected from the group consisting of frequency specific normalized spectral amplitude, spectral slope and spectral amplitude uncertainty;

computing at least one discriminant function from said at least two values, said function being computed according to a formula selected to provide discrimination among tissue types based on spectral characteristic values for signals reflected from tissues having known tissue types;

and identifying said tissue on the basis of the value of said discriminant function.

36. A method as specified in claim 35 wherein said analyzing step incudes deriving at least three spectral characteristics.

37. A method as specified in claim 35 or 36 wherein said computing step includes computing at least two discriminant functions.

38. A method for determining average particle size of scattering particles in a body of material, comprising:

transmitting acoustic signals into said material;

receiving reflected acoustic signals from at least a portion of said material;

analyzing said received signals to derive spectral data representative of spectral characteristics of said reflected signals;

normalizing said spectral data to values of said spectral data for an object with known reflection characteristics;

analyzing said normalized spectral data to derive spectral slope values thereof; and computing average particle size from said spectral slope values using a formula relating particle size to spectral slope.

39. A method as specified in claim 38 wherein said received signal is divided into signal time samples corresponding to areas of said body of material and wherein said particle size is computed for each of said areas.

40. A method as specified in claim 39 comprising a further step of generating a display having elemental display areas corresponding to said body areas and wherein said display areas are provided with a display characteristic according to said computed average particle size.

41. A method as specified in claim 1, 8, 9, 10, 17, 18, 22, 25, or 32 wherein the steps of said method are repeated at least two different times, and wherein the results of each final step are compared to detect any changes in the characteristics of said body.

42. A method as specified in claim 10, 16, 17, 22, 25, or 32 wherein the steps of said method are repeated after the tissue undergoes medical treatment.

43. A method as specified in claim 10, 16, 17, 22, 25, or 32 wherein the steps of said method are performed on tissue suspected of having disease, wherein the steps are repeated if disease is detected to determine the development of said disease, and wherein the tissue is subjected to medical treatment, and wherein the steps of said method are again repeated to determine the response of said tissue to said medical treatment.

* * * * *

UNITED STATES PATENT AND TRADEMARK OFFICE
CERTIFICATE OF CORRECTION

PATENT NO. : 4,858,124

DATED : August 15, 1989

INVENTOR(S) : FREDERIC L. LIZZI, ET AL.

It is certified that error appears in the above-identified patent and that said Letters Patent is hereby corrected as shown below:

First page, Item [73] should read --[73] Assignees: Riverside Research Institute, New York, NY, and Cornell Research Foundation, Inc., Ithaca, N.Y.--

First page, 4th line of Item [56], "6/1987" should read --6/1981--.

First page, 3rd from bottom line of ABSTRACT, "discriminent" should read --discriminant--.

Col. 4, line 20, after "melanoma" insert a semi-colon (;);

Col. 5, line 16, "results" should read --result--.

Col. 5, line 36, after "will" insert --be--.

Col. 6, line 10, "maybe" should read --may be--;

line 22, "maybe" should read --may be--;

line 49, "computer" should read --computed--.

Col. 7, line 17, after "slope," delete "amplitude";

line 18, after "spectral" insert --amplitude--.

UNITED STATES PATENT AND TRADEMARK OFFICE
CERTIFICATE OF CORRECTION

PATENT NO. : 4,858,124

DATED : August 15, 1989

INVENTOR(S) : FREDERIC L. LIZZI, ET AL.

It is certified that error appears in the above-identified patent and that said Letters Patent is hereby corrected as shown below:

Col. 9, line 9, "shown" should read --show--;

line 13, "characteristics" should read --characteristicline 63, "straining" should read --staining--;

line 66, "16ashows" should read --16a shows--;

line 68, "16bshows" should read --16b shows--.

Col. 10, line 1, "16astained" should read --16a stained--;

line 4, "16bcontains" should read --16b contains--;

line 7, "16cshows" should read --16c shows--; and "16astained" should read --16a stained--;

line 18, "17bshows" should read --17b shows--;

line 27, "preceeding" should read --preceding--;

line 34, "to" (first occurrence) should read --of--.

Col. 11, line 10, "disriminant" should read --discriminant--.

Col. 12, line 12, "bee" should read --been--;

line 45, after "transmitted" insert --signals--.

Col. 13, line 30, "comprise" should read --comprises--;

UNITED STATES PATENT AND TRADEMARK OFFICE
CERTIFICATE OF CORRECTION

PATENT NO.  : 4,858,124
DATED       : August 15, 1989
INVENTOR(S) : FREDERIC L. LIZZI, ET AL.

It is certified that error appears in the above-identified patent and that said Letters Patent is hereby corrected as shown below:

Col. 13, line 31, after "two" insert --sets--.

Col. 14, line 24, "clinicaly" should read --clinically--;

line 46, "regionof" should read --region of--;

line 64, after "two" insert --sets of--.

Col. 15, line 58, after "display" insert --of--.

Col. 17, line 31, "displaycharacteristic" should read --display characteristic-- line 34, "a" should read --as--.

Col. 18, line 34, "depthin" should read --depth in--.

Col. 20, line 27, "10," should read --16,--;
line 32, "claim 10," should read --claim 9,--;
line 35, "claim 10," should read --claim 9,--.

Signed and Sealed this

Seventh Day of August, 1990

*Attest:*

HARRY F. MANBECK, JR.

*Attesting Officer*   *Commissioner of Patents and Trademarks*